(12) United States Patent
Engel et al.

(10) Patent No.: US 10,830,745 B2
(45) Date of Patent: Nov. 10, 2020

(54) MINIATURIZED PRECISION AGRICULTURE

(71) Applicant: International Business Machines Corporation, Armonk, NY (US)

(72) Inventors: Michael Engel, Rio de Janeiro (BR); Ademir Ferreira da Silva, Sao Paulo (BR); Ado Jorio de Vasconcelos, Belo Horizonte (BR); Ricardo L. Ohta, Sao Paulo (BR); Mathias B. Steiner, Rio de Janeiro (BR)

(73) Assignees: International Business Machines Corporation, Armonk, NY (US); UNIVERSIDADE FEDERAL DE MINAS GERAIS (UFMG), Belo Horizonte (BR)

( * ) Notice: Subject to any disclaimer, the term of this patent is extended or adjusted under 35 U.S.C. 154(b) by 345 days.

(21) Appl. No.: 15/853,884

(22) Filed: Dec. 25, 2017

(65) Prior Publication Data
US 2019/0195851 A1    Jun. 27, 2019

(51) Int. Cl.
*G01N 33/00*    (2006.01)
*G01N 21/84*    (2006.01)
*A01G 9/02*    (2018.01)

(52) U.S. Cl.
CPC ........... *G01N 33/0098* (2013.01); *A01G 9/02* (2013.01); *G01N 21/84* (2013.01); *G01N 2021/8466* (2013.01)

(58) Field of Classification Search
USPC ......... 47/56, 61, 60, 65, 65.5, 66.5, 66.7, 69
See application file for complete search history.

(56) References Cited

U.S. PATENT DOCUMENTS 4,979,332 A * 12/1990 Nagaya ............... A01G 9/02
                                                          47/69
5,224,598 A *  7/1993 Angeles ................ B65D 85/52
                                                         206/423

(Continued)

FOREIGN PATENT DOCUMENTS

WO     2005105292 A1    11/2005
WO     2012091540 A1     7/2012

OTHER PUBLICATIONS

Peter Mell et al., "The NIST Definition of Cloud Computing". Special Publication 800-145. NIST. Sep. 2011, pp. 1-7.

(Continued)

*Primary Examiner* — Andrea M Valenti
(74) *Attorney, Agent, or Firm* — Joseph Petrokaitis; Otterstedt, Wallace & Kammer, LLP (57) ABSTRACT

A growth chamber chip includes a base surrounding a growth chamber; a growth medium within the growth chamber; a sensor package within the growth chamber; a sensor feedthrough extending from the sensor package through a portion of the base to an outer surface of the base; and a transparent seal covering the growth chamber. In one or more embodiments, the base includes a nutrient channel connected in fluid communication with the growth medium and exposed to an outer surface of the base. One or more embodiments provide an array of growth chamber chips, with a movable arm that is movable across the array to individually scan each of the growth chamber chips.

6 Claims, 10 Drawing Sheets

(56) References Cited

U.S. PATENT DOCUMENTS

| | | | |
|---|---|---|---|
| 7,682,103 B2* | 3/2010 | Byles | A01G 9/00 405/45 |
| 7,691,623 B2 | 4/2010 | Jobst et al. | |
| 8,251,017 B2* | 8/2012 | Ridgway | C05F 17/05 119/452 |
| 9,199,238 B2 | 12/2015 | Koltzscher et al. | |
| 9,375,712 B2 | 6/2016 | Durniak et al. | |
| 9,629,313 B1* | 4/2017 | Grossman | A01G 25/16 |
| 9,643,181 B1 | 5/2017 | Chang et al. | |
| 10,234,876 B2* | 3/2019 | Grossman | G05D 7/0617 |
| 10,470,379 B1* | 11/2019 | Dong | A01C 1/02 |
| 2009/0161102 A1* | 6/2009 | Deppermann | G01N 21/31 356/303 |
| 2010/0199734 A1* | 8/2010 | Bottcher | C05D 9/00 71/8 |
| 2011/0237445 A1 | 9/2011 | Andersson Svahn et al. | |
| 2013/0275426 A1 | 10/2013 | Minvielle | |
| 2014/0326029 A1* | 11/2014 | Hashaikeh | C05G 3/04 71/1 |
| 2015/0015697 A1* | 1/2015 | Redden | G01N 33/0098 348/89 |
| 2015/0081058 A1* | 3/2015 | Oliver | A63F 13/245 700/91 |
| 2016/0129455 A1 | 5/2016 | Wang et al. | |
| 2019/0033210 A1* | 1/2019 | Yarden | B07C 5/342 |
| 2019/0183062 A1* | 6/2019 | Pham | A01G 9/0297 |

OTHER PUBLICATIONS

John E. Kelly III, "Computing, cognition, and the future of knowing", IBM Corp. Oct. 2015. pp. 1-7.

Unknown, "Barometric pressure sensors", Servoflo Corporation, downloaded from the Internet Nov. 2017, pp. 1-24.

Unknown, "Datasheet SHT20P Humidity and Temperature Sensor IC", Sensirion AG, May 2014, pp. 1-10.

Unknown, "HDC1000 low power, high accuracy digital humidity sensor with temperature sensor", Texas Instruments, Jan. 2016, pp. 1-31.

David Erickson et al., "Smartphone technology can be transformative to the deployment of lab-on-chip diagnostics", Lab Chip 2014 (Mar. 2014). v. 14 pp. 3159-3164.

Huawei Jiang et al., "Plant chip for high-throughput phenotyping of *Arabidopsis*", Lab Chip 2014 (Jan. 2014). v. 14 pp. 1281-1293.

George Luka et al., "Microfluidics integrated biosensors: a leading technology towards lab-on-a-chip and sensing applications". Sensors 2015 (Dec. 2015), v. 15, pp. 30011-30031.

A. Peix et al., "Growth promotion of chickpea and barley by a phosphate solubilizing strain of Mesorhizobium mediterraneum under growth chamber conditions." Soil Biology and Biochemistry 33.1 (Jan. 2001): pp. 103-110.

J.R. De Freitas et al. "Growth promotion of winter wheat by fluorescent pseudomonads under growth chamber conditions". Soil Biology and biochemistry 24(11) (Nov. 1992). pp. 1127-1135.

* cited by examiner

MINIATURIZED PRECISION AGRICULTURE

BACKGROUND

The present invention relates to electronics and to agriculture, and more specifically, to a miniaturized growth chamber on a chip complete with an electronic sensor package.

In order to obtain information regarding the germination and growth of plants under various conditions, seeds can be sown in greenhouses or in growth chambers with controlled environmental and nutritional variables. For example, a greenhouse can be maintained within a temperature range of about five degrees Celsius; a growth chamber can be maintained within a temperature range of a few degrees Celsius. Nutritional variables can include controlled drip rates of minerals and other nutrients in aqueous solution. Once the growing plants have reached the seedling stage, they can be observed and measured by conventional techniques, such as visual observation and measurement using a ruler, in order to identify growth rates and locations of structures such as cotyledons and first leaves.

SUMMARY

Principles of the invention provide techniques for miniaturized precision agriculture. In one aspect, an exemplary method includes providing a growth chamber chip equipped with a growth medium and a sensor package, depositing a seed on the growth medium, exposing the growth chamber chip to environmental conditions conducive to seed germination, and connecting the sensor package in communication with a processing and communications package. In one or more embodiments, the exemplary method further includes using a camera of the processing and communications package to obtain images of the seed on the growth medium.

In another aspect, an exemplary embodiment of the invention provides a growth chamber chip, which includes a base surrounding a growth chamber; a growth medium within the growth chamber; a sensor package within the growth chamber; a sensor feedthrough extending from the sensor package through a portion of the base to an outer surface of the base; and a transparent seal covering the growth chamber.

In another aspect, an exemplary embodiment of the invention provides a growth chamber chip and an input/output communications apparatus. The growth chamber chip includes a base surrounding a growth chamber; a growth medium within the growth chamber; a sensor package within the growth chamber; a sensor feedthrough extending from the sensor package through a portion of the base to an outer surface of the base; and a transparent seal covering the growth chamber. The input/output communications apparatus includes a frame assembled over the base; an internal communications package housed on the frame and connected in communication with the sensor feedthrough of the base; and a camera-equipped processing and external communications package (CEPECP) housed on the frame and connected in communication with the internal communications package and in communication with a cloud service.

In another aspect, an exemplary embodiment of the invention provides a growth chamber chip and a movable arm. The growth chamber chip includes a base surrounding a growth chamber; a growth medium within the growth chamber; a sensor package within the growth chamber; a sensor feedthrough extending from the sensor package through a portion of the base to an outer surface of the base; and a transparent seal covering the growth chamber. The movable arm is suspended above the base and includes a camera housed on the movable arm; an internal communications package housed on the movable arm and connected in communication with the sensor feedthrough of the base; and a camera-equipped processing and external communications package housed on the movable arm and connected in communication with the internal communications package and in communication with a cloud service.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

In view of the foregoing, techniques of the present invention can provide substantial beneficial technical effects. For example, one or more embodiments provide one or more of:

A holistic solution for miniaturized precision agriculture that allows for systematic studies of early stage seed growth under controlled conditions.

Massively parallel studies of single seed growth under different conditions.

Function as an incubator space, i.e., after initial germination the specimen can be transferred into field.

Speed up assessment of genetically modified seeds to identify superior modifications.

These and other features and advantages of the present invention will become apparent from the following detailed description of illustrative embodiments thereof, which is to be read in connection with the accompanying drawings.

DETAILED DESCRIPTION

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
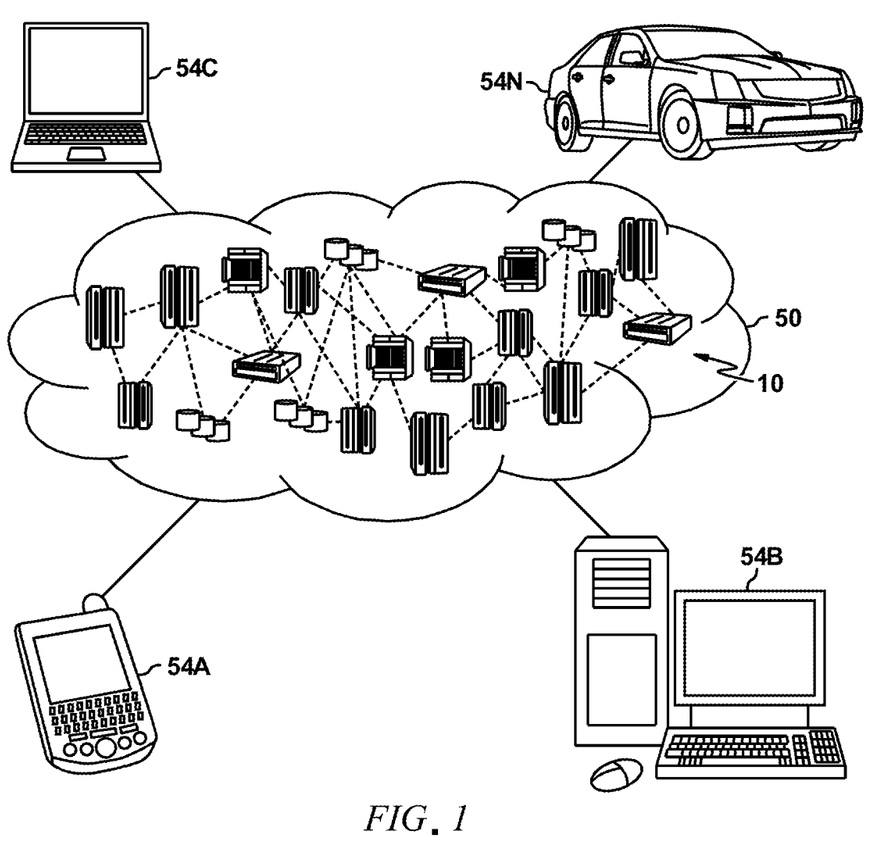
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
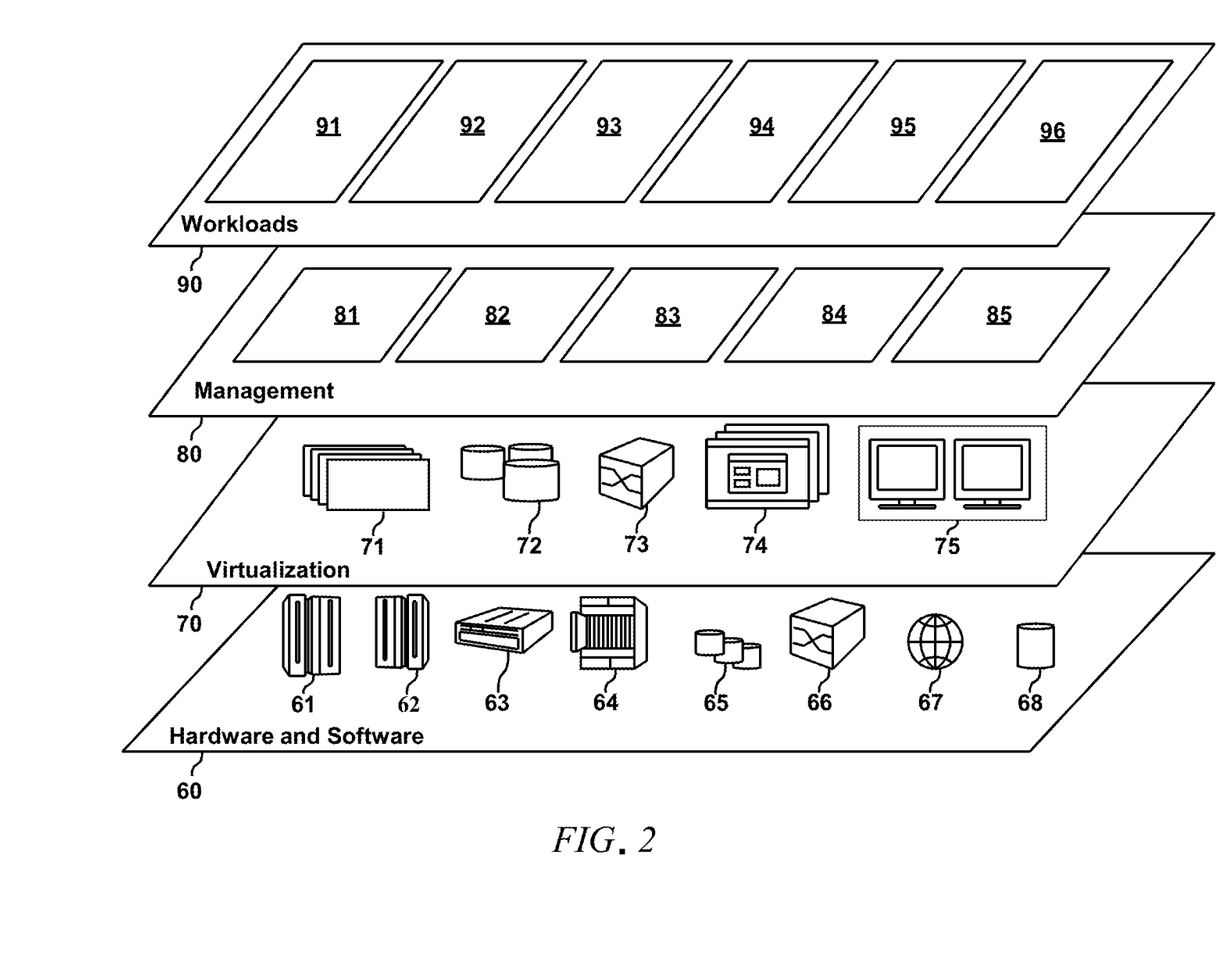
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a miniaturized precision agriculture cloud service 96, which will be further discussed below with reference to FIG. 8.

Figure 3:
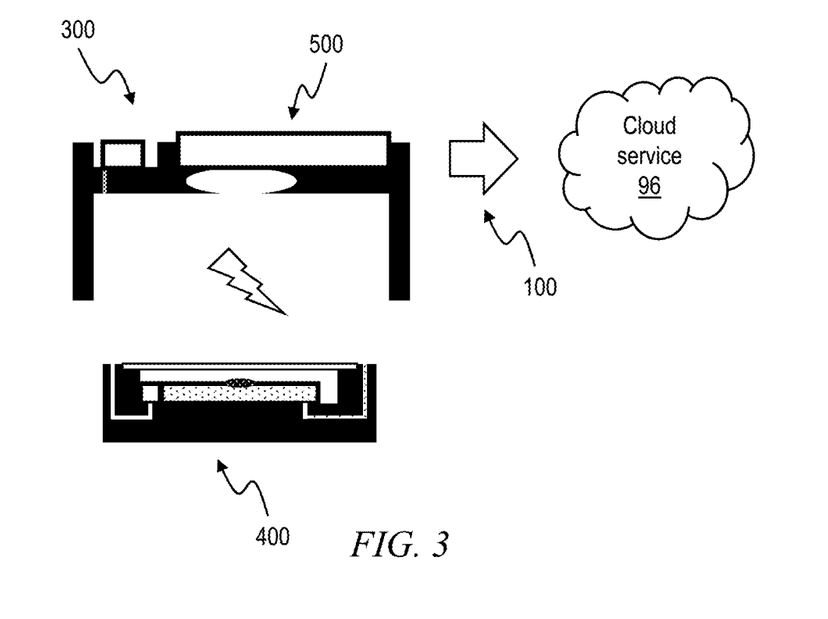
FIG. 3 depicts a block diagram of an exemplary embodiment of the inventive system for miniaturized precision agriculture.

Generally, FIG. 3 depicts a block diagram of an exemplary embodiment 300 of the inventive system for miniaturized precision agriculture. The exemplary system 300 includes a growth chamber chip 400, an input/output communications apparatus 500, and the miniaturized precision agriculture cloud service 96. The growth chamber chip 400 is connected in communication with the cloud service 96 via the input/output communications apparatus 500, which connects with the cloud service 96 via an Internet connection 100.

Figure 4:
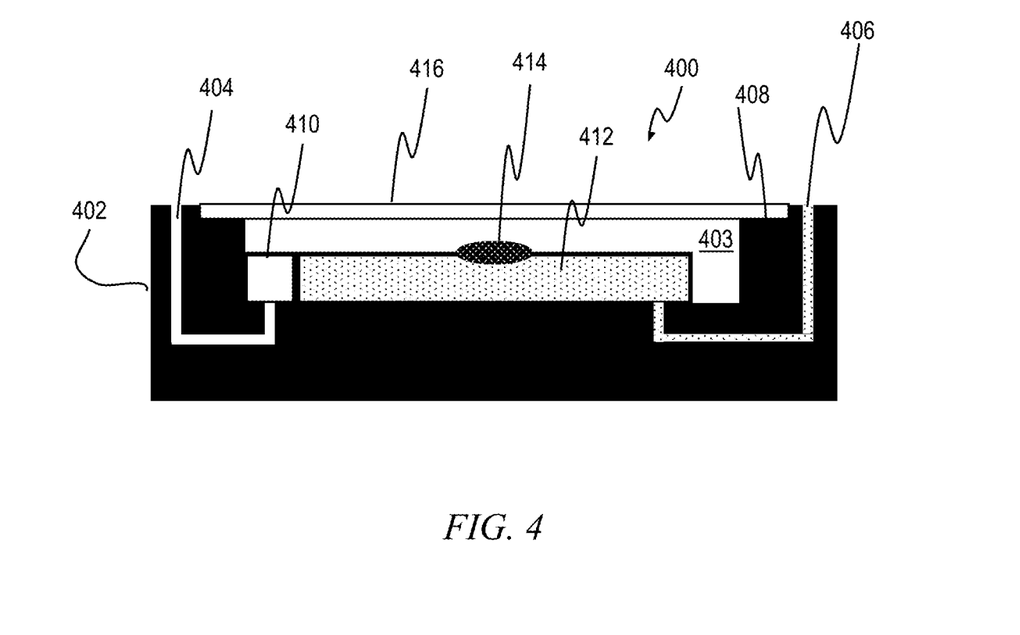
FIG. 4 depicts components of a growth chamber chip, according to an exemplary embodiment.

FIG. 4 depicts components of the exemplary growth chamber chip 400. The growth chamber chip 400 includes a base 402, which surrounds a growth chamber 403. A sensor feedthrough 404, a nutrient channel 406, and a ledge 408 are formed in the base 402. A sensor package 410 is placed into the growth chamber 403 in electrical communication with the sensor feedthrough 404. A nutrient reservoir/growth medium 412 is placed into the growth chamber 403 adjacent to the sensor package 410 and in fluid communication with the nutrient channel 406. Although the growth medium 412 is shown alongside the sensor package 410, in other embodiments (not shown) the growth medium 412 can be positioned above, below, or even surrounding the sensor package 410. A seed 414 is placed onto the growth medium 412, and a transparent seal 416 is affixed at the ledge 408 to enclose the growth chamber 403. In one or more embodiments, a total footprint of the growth chamber chip 400 is less than 1 centimeter (cm) square, e.g., between 5 and 10 millimeters (mm) on a side.

The sensor package 410 includes, for example, temperature, pressure, and humidity sensors. One exemplary temperature/humidity sensor can be obtained from Texas Instruments Incorporated as the HDC1000 package. Another exemplary temperature/humidity sensor can be obtained from Sensirion AG as the SHT20P package. Pressure can be sensed by piezoelectrics. For example, an integrated pressure/temperature/humidity sensor package can be obtained from Servoflo Corporation as the MS8607 package.

In one or more embodiments, the growth medium 412 may include, for example, nutrient loaded micro-cellulose, terra preta, or other relatively nutrient-rich porous media. In other embodiments, the growth medium 412 may be a nutrient-depleted substance for observation of seed hardiness in unfavorable conditions.

Figure 5:
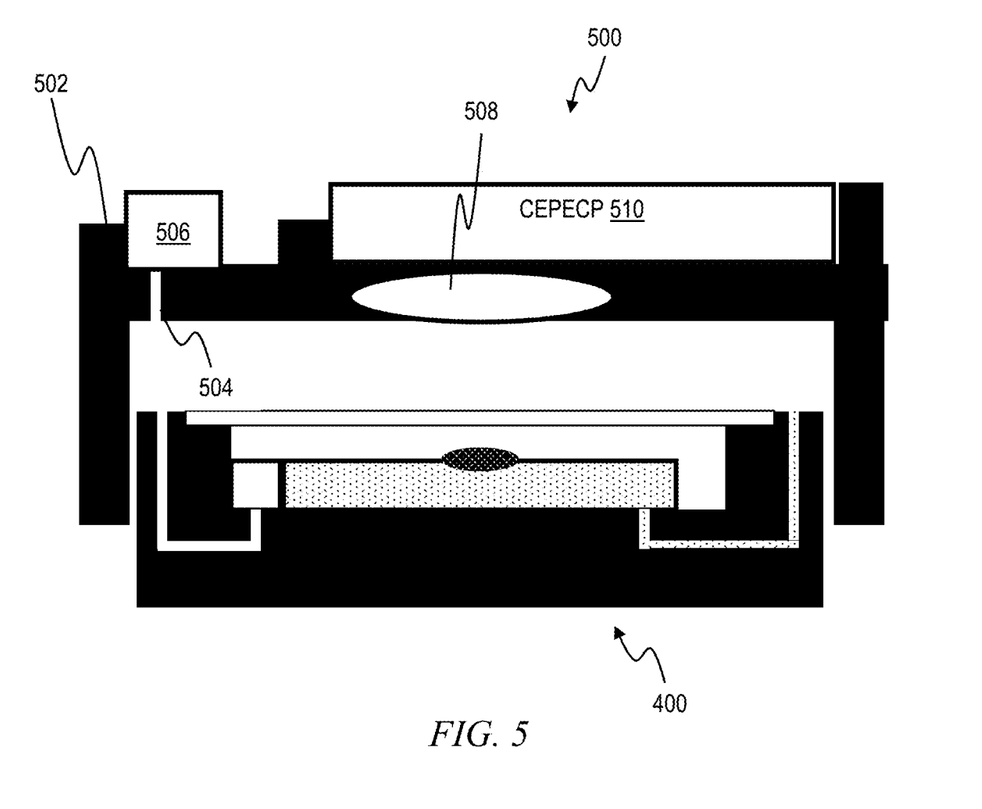
FIG. 5 depicts an input/output communications apparatus juxtaposed with a growth chamber chip, according to an exemplary embodiment.

FIG. 5 depicts the input/output communications apparatus 500 juxtaposed with the exemplary growth chamber chip 400. The input/output communications apparatus 500 includes a frame 502, a sensor feedthrough 504, an internal communications package 506, an optical element 508, and a camera-equipped processing and external communications package ("CEPECP") 510. The CEPECP 510 could include, in one or more embodiments, a smartphone or a customized hardware such as a RASPBERRY PI or ARDUINO kit. Not shown are one or more fluid connections for supplying nutrients through the frame 502 to the nutrient channel 406 of the growth chamber chip 400.

The frame 502 fits over the growth chamber chip 400 so that the optical element 508 and the camera of the CEPECP 510 are aligned to the growth medium 412 within the growth chamber 403, while the sensor feedthrough 504 is connected in electrical communication with the sensor feedthrough 404 of the growth chamber chip 400. In one or more embodiments, a specification for the sensor feedthroughs 404 and 504 is the Micro-USB standard promulgated by the USB Implementers Forum, Inc. Other specifications and standards will be apparent to the skilled worker.

The internal communications package 506 wirelessly connects the sensor feedthrough 504 in communication with the CEPECP 510. In one or more embodiments, specifications for the internal communications package 506 are Micro-USB and the BLUETOOTH™ standard promulgated by Bluetooth SIG, Inc. Other specifications and standards will be apparent to the skilled worker.

The optical element 508 is a transparent portion of the frame 502. In one or more embodiments, the optical element 508 magnifies the view of the seed 414 to enable detection of small features otherwise undistinguishable by the camera of the CEPECP 510. The CEPECP 510 is mounted to the frame 502 with its camera aligned to the optical element 508.

Figure 6:
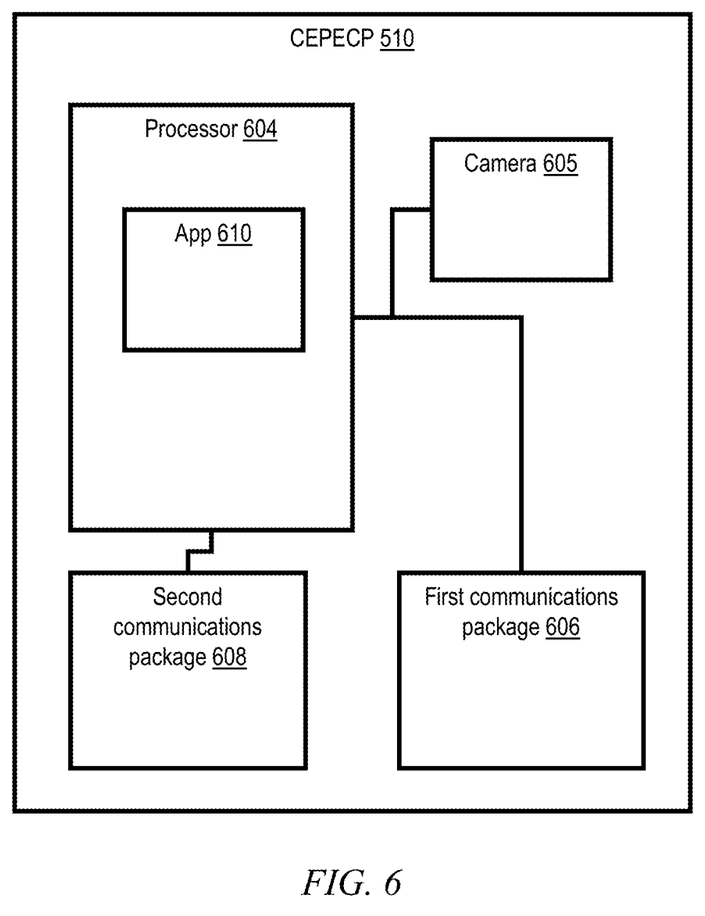
FIG. 6 depicts details of a camera-equipped processing and external communications package ("CEPECP") for use in the input/output communications apparatus of FIG. 5, according to an exemplary embodiment.

The CEPECP 510 is shown in greater detail in FIG. 6. It includes a body 602, a processor 604, the camera 605, a first communications package 606 that can be connected in wired or wireless communication with the internal communications package 506 according to the same standard, and a second communications package 608 that can be connected in wired or wireless communication with the Internet connection 100 according to a standard such as the 4G LTE standard promulgated by the International Telecommunications Union. The processor 604 communicates with the camera 605 and with both the first and second communications packages 606, 608. The processor 604 implements an app 610 that manipulates image data from the camera 605 and sensor data from the first communications package 606 and passes the data through the second communications package 608.

Figure 7:
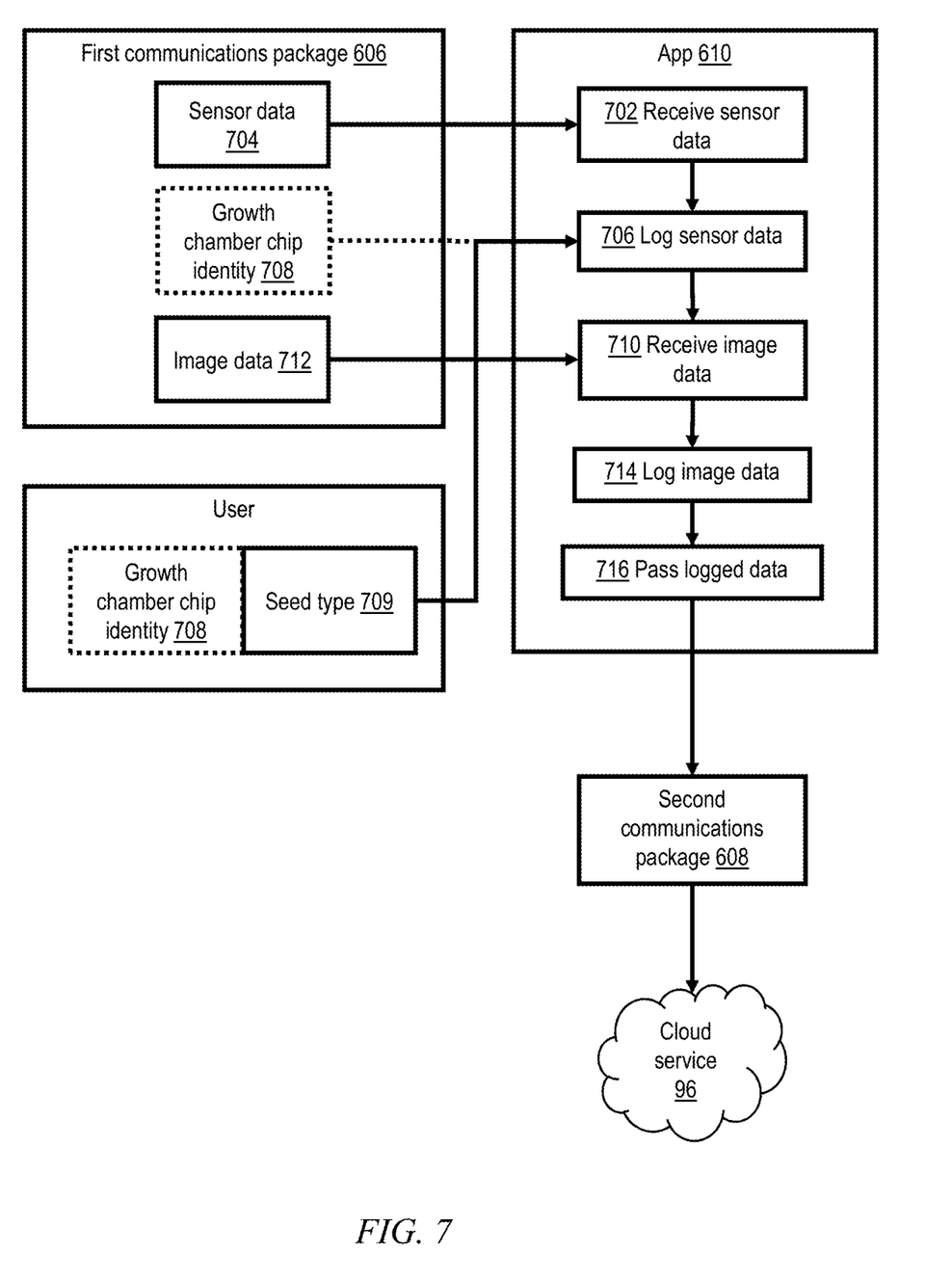
FIG. 7 depicts functionality of an app implemented by the CEPECP of FIG. 6.

FIG. 7 depicts functionality of the app 610. At block 702 the app 610 receives sensor data 704 from the first communications package 606. The sensor data 704 includes, for example, temperature, pressure, and humidity of the growth chamber 403. At block 706 the app 610 logs the sensor data 704 in association with an identity 708 of the growth chamber chip 400; this is helpful in case the input/output communications apparatus 500 and the app 610 are being used to monitor conditions of multiple growth chamber chips. In one or more embodiments, the internal communications package 506 supplies the identity 708 as a unique binary sequence. Alternatively, a user of the app may provide the identity 708 as well as a seed type 709. At block 710 the app 610 receives image data 712 from the camera 605. The image data 712 shows the condition of the seed or seedling 414 within the growth chamber 403. At block 714 the app 610 logs the image data 712 in association with the growth chamber chip identity 708. At block 716 the app 610 passes the logged data 704, 708, 712 through the second communications package 608 and the Internet connection to the cloud service 96.

Figure 8:
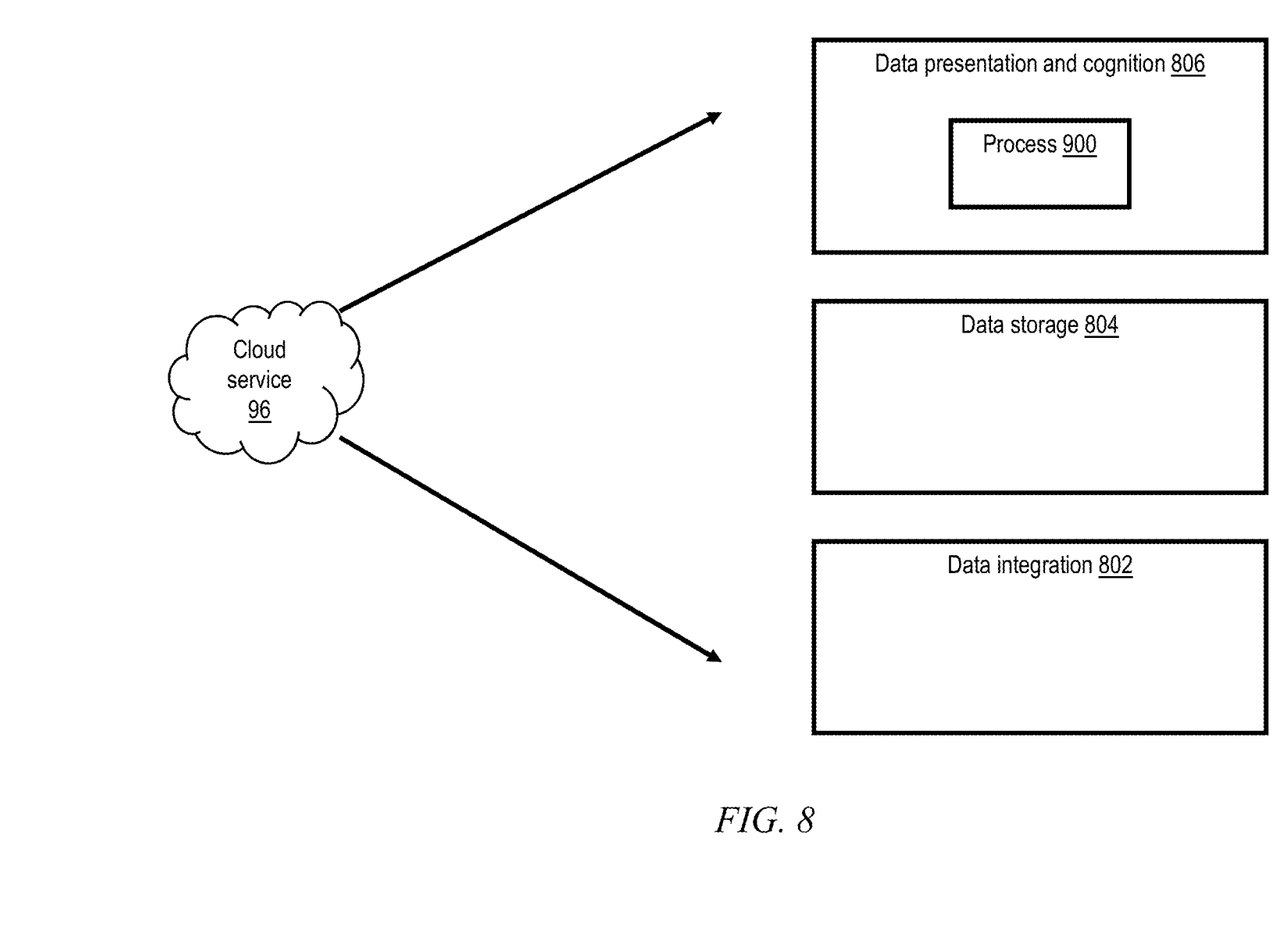
FIG. 8 depicts functionality of a miniaturized precision agriculture cloud service that is implemented within the exemplary system of FIG. 3.

FIG. 8 depicts functionality of the miniaturized precision agriculture cloud service 96. Generally, the cloud service 96 performs data gathering, storage, visualization and analysis. Data gathering is done by light weight protocols suitable for Internet of Things (IoT) applications or HTTP/HTTPS protocols, by using a standardized API interface. Data storage is accomplished by a cloud database, which is distributed for multi-application scenarios. In one or more embodiments, the cloud service 96 is built in a Platform as a Service (PaaS) model, giving flexibility in terms of scalability and features. The cloud service 96 provides easy visualization in a web interface, by which specialists can leverage the gathered data to generate reports.

Thus, the miniaturized precision agriculture cloud service 96 provides layers of different purposes to provide the functionality of data gathering, persistence, visualization, clustering and data analysis capabilities. Clients such as web browsers, mobile applications, servers, etc., can consume the data of this computing service, facilitating ubiquitous and pervasive access to information. In one or more embodiments, this computational infrastructure is subdivided into several layers: data integration 802, data storage 804, and data presentation and cognition 806.

The data integration layer 802 performs the reception and transmission of data packets to and from the CEPECP 510. These data packets can represent text messages, images, videos or other events. In one or more embodiments, the data integration layer 802 is implemented via the IBM Watson Internet of Things (IoT) Platform cloud service, from IBM Cloud PaaS (Platform as a Service), which uses telemetry messaging protocols such as MQTT (Message Queuing Telemetry Transport).

The data storage layer 804 provides data persistence. In certain embodiments, the data storage layer 804 is implemented via structured-mode (SQL) or unstructured (NoSQL) database platforms, for example, IBM DB2, IBM Cloudant, or MongoDB.

The data presentation and cognition layer 806 provides visualization of data gathering by Web application, mobile application update service, data queries, statistical and/or visual trends of data interpretations, and automatic cognitive insights. Certain implementations of the data cognition layer 806 make use of cognitive neural networks.

Generally, a cognitive neural network includes a plurality of computer processors that are configured to work together to implement one or more machine learning algorithms. The implementation may be synchronous or asynchronous. In a neural network, the processors simulate thousands or millions of neurons, which are connected by axons and synapses. Each connection is enforcing, inhibitory, or neutral in its effect on the activation state of connected neural units. Each individual neural unit has a summation function which combines the values of all its inputs together. In some implementations, there is a threshold function or limiting function on at least some connections and/or on at least some neural units, such that the signal must surpass the limit before propagating to other neurons. A cognitive neural network can implement supervised, unsupervised, or semi-supervised machine learning.

Figure 9:
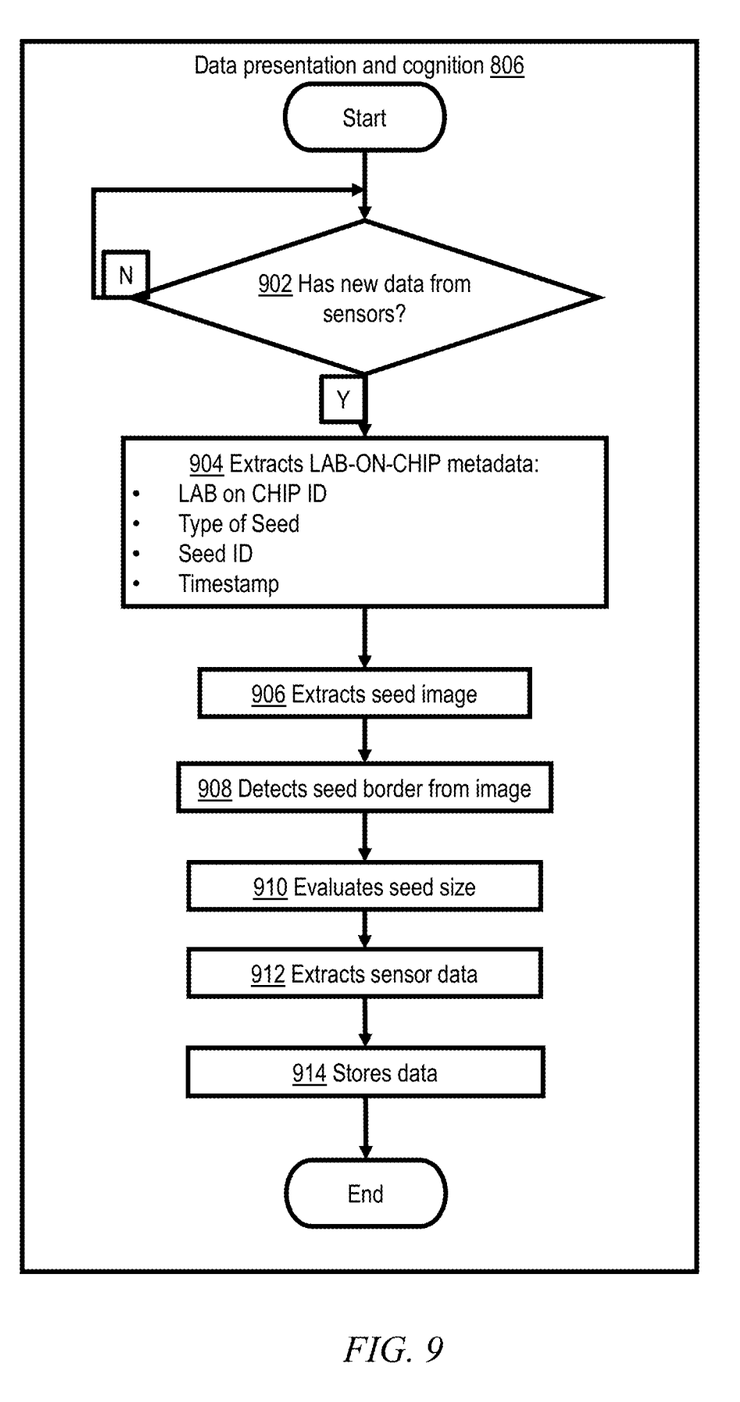
FIG. 9 depicts further functionality of the cloud service of FIG. 8.

In certain aspects, the data cognition layer 806 implements a process 900 as shown in FIG. 9. At block 902 the data cognition layer 806 checks whether new data has been received from sensors of the input/output communications apparatus 500. At block 904, in case new data has been received, the data cognition layer 806 extracts lab-on-chip metadata including chip identity, type of seed, seed identity, and a timestamp. At block 906 the data cognition layer 806 extracts a seed image. At block 908 the data cognition layer 806 makes use of a cognitive neural network/similar artificial intelligence technique (e.g., a support vector machine) or image processing algorithm to detect a seed border in the seed image. At block 910 the data cognition layer 806 evaluates a size of the seed based on the seed image. At block 912 the data cognition layer 806 extracts sensor data such as temperature, pressure, and humidity. At block 914 the data cognition layer 806 stores the extracted sensor data along with the size of the seed, the timestamp, etc.

Figure 10:
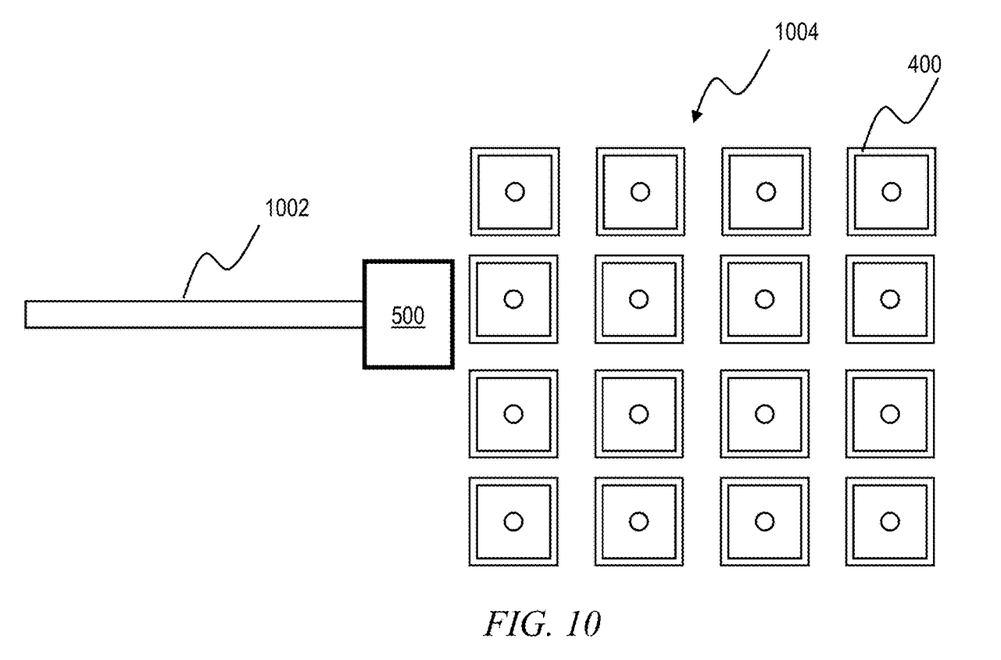
FIG. 10 depicts an input/output communications apparatus mounted on a movable arm in conjunction with a massively parallel array of growth chamber chips, according to an exemplary embodiment.

FIG. 10 depicts an exemplary embodiment in which an input/output communications apparatus 500 is mounted on a movable arm 1002 in conjunction with a massively parallel array 1004 of growth chamber chips 400. The movable arm 1002 sequentially positions the input/output communications apparatus 500 above each of the growth chamber chips 400 so that the conditions of the particular chip can be read and transmitted to the cloud service 96. As in FIG. 5, the input/output communications apparatus includes a frame, an internal communications package, a CEPECP, and an optical element. Unlike in FIG. 5, the frame of the input/output communications apparatus 500 does not fit over the growth chamber chips 400. Instead, the frame is flat-bottomed to permit scanning it quickly across the chips array 1004.

Generally, embodiments of the invention can be employed in a method for studying the germination of seeds. In one or more embodiments, an exemplary method includes providing a growth chamber chip equipped with a growth medium and a sensor package, depositing a seed on the growth medium, exposing the growth chamber chip to environmental conditions conducive to seed germination, and connecting the sensor package in communication with a processing and communications package. In one or more embodiments, the exemplary method further includes using a camera of the processing and communications package to obtain images of the seed on the growth medium. In one or more embodiments, the exemplary method further includes connecting the processing and communications package in communication with a cloud service that can employ cognitive neural networks, image processing, or other artificial intelligence to monitor seed germination and growth rates based on the images obtained by the camera. In one or more embodiments, the exemplary method further includes providing growth chamber chip identity and seed type to the cloud service along with the images and data from the sensor package.

Given the discussion thus far, it will be appreciated that, in general terms, an exemplary embodiment of the invention provides a growth chamber chip, which includes a base surrounding a growth chamber; a growth medium within the growth chamber; a sensor package within the growth chamber; a sensor feedthrough extending from the sensor package through a portion of the base to an outer surface of the base; and a transparent seal covering the growth chamber. In one or more embodiments, the base includes a nutrient channel connected in fluid communication with the growth medium and exposed to an outer surface of the base. In one or more embodiments, the growth medium includes terra preta. In one or more embodiments, the growth medium includes nutrient-enriched microcellulose. One or more embodiments further provide a seed contacting the growth medium. In one or more embodiments, the sensor package includes temperature, pressure, and humidity sensors.

Another exemplary embodiment of the invention provides a growth chamber chip and an input/output communications apparatus. The growth chamber chip includes a base surrounding a growth chamber; a growth medium within the growth chamber; a sensor package within the growth chamber; a sensor feedthrough extending from the sensor package through a portion of the base to an outer surface of the base; and a transparent seal covering the growth chamber. The input/output communications apparatus includes a frame assembled over the base; an internal communications package housed on the frame and connected in communication with the sensor feedthrough of the base; and a camera-equipped processing and external communications package (CEPECP) housed on the frame and connected in communication with the internal communications package and in communication with a cloud service. In one or more embodiments, the base includes a nutrient channel connected in fluid communication with the growth medium and exposed to an outer surface of the base. In one or more embodiments, the CEPECP includes a first communications package connected in communication with the internal communications package and a second communications package connected in communication with the cloud service. One or more embodiments of the input/output communications apparatus include an optical element housed in the frame, wherein a camera of the CEPECP is aligned to the optical element and the camera and the optical element are aligned to the growth medium. One or more embodiments further include a seed contacting the growth medium. In one or more embodiments, the sensor package includes temperature, pressure, and humidity sensors.

Another exemplary embodiment of the invention provides a growth chamber chip and a movable arm. The growth chamber chip includes a base surrounding a growth chamber; a growth medium within the growth chamber; a sensor package within the growth chamber; a sensor feedthrough extending from the sensor package through a portion of the base to an outer surface of the base; and a transparent seal covering the growth chamber. The movable arm is suspended above the base and includes a camera housed on the movable arm; an internal communications package housed on the movable arm and connected in communication with the sensor feedthrough of the base; and a camera-equipped processing and external communications package housed on the movable arm and connected in communication with the internal communications package and in communication with a cloud service. In one or more embodiments, the base includes a nutrient channel connected in fluid communication with the growth medium and exposed to an outer surface of the base. In one or more embodiments, the CEPECP includes a first communications package connected in communication with the internal communications package and a second communications package connected in communication with the cloud service. In one or more embodiments, the movable arm includes an optical element housed in the movable arm, wherein a camera of the CEPECP is aligned to the optical element and the camera and the optical element are aligned to the growth medium. One or more embodiments further include a seed contacting the growth medium. In one or more embodiments, the sensor package includes temperature, pressure, and humidity sensors. One or more embodiments provide an array of growth chamber chips, wherein the movable arm is movable across the array to individually scan each of the growth chamber chips. In one or more embodiments, each of the growth chamber chips is encoded with an individual identity code.

Figure 11:
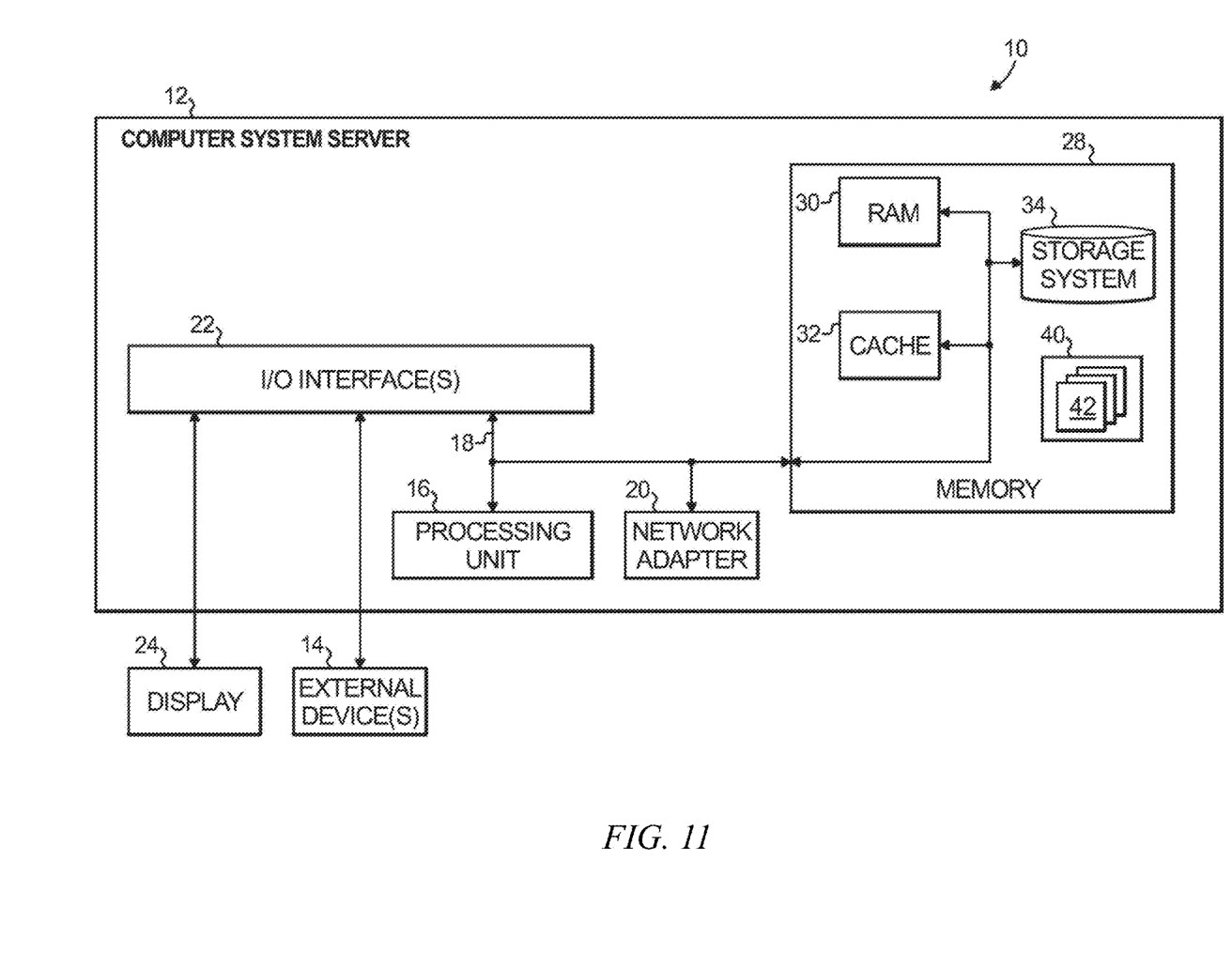
FIG. 11 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps, or in the form of a non-transitory computer readable medium embodying computer executable instructions which when executed by a computer cause the computer to perform exemplary method steps. FIG. 11 depicts a computer system that may be useful in implementing one or more aspects and/or elements of the invention, also representative of a cloud computing node according to an embodiment of the present invention. Referring now to FIG. 11, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 11, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 11, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 11) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An agriculture apparatus comprising:
a growth chamber chip comprising:
a base that has a base sidewall surrounding a growth chamber that is configured to receive a seed;
a growth medium within the growth chamber; a seed deposited on the growth medium;
a sensor package within the growth chamber;
a sensor feedthrough extending from the sensor package through a portion of the base to an outer surface of the base; and
a transparent seal covering the growth chamber; and
an input/output communications apparatus comprising:
a frame that has a frame sidewall, which is positioned directly parallel to the base sidewall and directly fittingly attaches the frame over a top edge of the base sidewall, wherein the frame includes a planar member that extends over the base perpendicular to the base sidewall and the frame sidewall and that houses a magnifying optical element aligned to the transparent seal, wherein the magnifying optical element comprises a transparent portion of the frame;
an internal communications package housed on the frame and connected in communication with the sensor feedthrough of the base; and
a camera-equipped processing and external communications package (CEPECP) housed on the frame and connected in communication with the internal communications package and in communication with a cloud service, wherein a camera of the CEPECP is aligned to the magnifying optical element, wherein the magnifying optical element is discrete from any lens of the camera.

2. The apparatus of claim 1 wherein the growth medium includes terra preta.

3. The apparatus of claim 1 wherein the growth medium includes nutrient-enriched microcellulose.

4. The apparatus of claim 1 wherein the base includes a nutrient channel connected in fluid communication with the growth medium and exposed to an outer surface of the base.

5. The apparatus of claim 1 wherein the CEPECP includes a first communications package connected in communication with the internal communications package and a second communications package connected in communication with the cloud service.

6. The apparatus of claim 1 wherein the sensor package includes temperature, pressure, and humidity sensors.

* * * * *